United States Patent
Demharter et al.

(10) Patent No.: US 7,899,521 B2
(45) Date of Patent: Mar. 1, 2011

(54) EKG MEASUREMENT DEVICE

(75) Inventors: Nikolaus Demharter, Dormitz (DE); Michael Frank, Erlangen (DE); Sven Heggen, Erlangen (DE); Jürgen Rössler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 182 days.

(21) Appl. No.: 12/284,690

(22) Filed: Sep. 24, 2008

(65) Prior Publication Data

US 2009/0088654 A1    Apr. 2, 2009

(30) Foreign Application Priority Data

Sep. 28, 2007    (DE) .................. 10 2007 046 510

(51) Int. Cl.
*A61B 5/02*    (2006.01)

(52) U.S. Cl. .................................... 600/509

(58) Field of Classification Search ............. 600/509, 600/521

See application file for complete search history.

(56) References Cited

U.S. PATENT DOCUMENTS

| | | | | | |
|---|---|---|---|---|---|
| 4,548,204 | A | * | 10/1985 | Groch et al. | 600/513 |
| 5,228,450 | A | * | 7/1993 | Sellers | 600/524 |
| 5,379,766 | A | * | 1/1995 | McKinnon et al. | 600/413 |
| 2002/0183635 | A1 | | 12/2002 | Yonce | |
| 2007/0179376 | A1 | | 8/2007 | Gerder | |

FOREIGN PATENT DOCUMENTS

DE    10 2006 004 683 A1    8/2007

\* cited by examiner

*Primary Examiner*—Carl H Layno
*Assistant Examiner*—Brian T Gedeon

(57) ABSTRACT

The invention relates to an EKG measurement device. The EKG measurement device comprises a number of EKG electrodes and a common-mode measurement unit connected on its input side to the EKG electrodes. Inventively an EKG trigger unit is connected on its input side to the EKG electrodes and to the common-mode measurement unit.

10 Claims, 6 Drawing Sheets

EKG MEASUREMENT DEVICE

CROSS REFERENCE TO RELATED APPLICATIONS

This application claims priority of German application No. 10 2007 046 510.8 filed Sep. 28, 2007, which is incorporated by reference herein in its entirety.

FIELD OF THE INVENTION

The invention relates to an EKG measurement device with a number of EKG electrodes and with a common-mode measurement unit connected on its input side to the EKG electrodes.

BACKGROUND OF THE INVENTION

An EKG measurement device typically receives an EKG signal with two EKG electrodes that are connected to inputs of a high-impedance differential amplifier. If there is the option of connecting more than two EKG electrodes to the EKG measurement device, typically one of the EKG electrodes will be used as a common reference point.

An EKG measurement device of the type mentioned above is disclosed in the book by Karsten Meyer-Waarden: "Bioelektrische Signale und ihre Ableitverfahren (Bioelectric signals and their derivation process)", 1985, Schattauer Verlagsgesellschaft, Stuttgart, Germany, on pages 142 to 143. In the EKG measurement device described therein a noise signal with a common-mode component is reduced at two EKG measurement electrodes with the so-called reference potential control method. The noise signal is created by a displacement current which is produced in its turn here by an electrical power supply network with alternating current. In the reference potential control method the reference electrode is not at reference ground or reference potential, but receives a potential corresponding to the common-mode component of the noise signal. The noise signal is tapped off at the two EKG electrodes. The common-mode component of the noise signal is fed, after amplification, impedance conversion and inversion, to the electrode which determines the reference potential for the measurement. The displacement current coupled into the body thus does not flow against the reference ground at a constant reference potential but flows into a reference point of which the potential is controlled by the noise voltage. The displacement current is compensated for by an opposing current in terms of amount and phase.

EKG devices are used not only for measurement and monitoring of the heart function but also in medical imaging to create trigger signals. Information about the heart phase is obtained from the EKG signal during imaging in order in this way to synchronize the imaging with the heart activity. With imaging processes requiring a longer period to record the image in particular high-quality images of the heart or also images of regions which pulse with the beating of the heart can be created.

EKG measurement devices are therefore also advantageous for in-situ recording of EKG signals during an examination of a patient by means of a magnetic resonance (MR) device. Operation in the magnetic resonance device however demands a series of measures to make trouble-free measurement in the environment of the magnetic resonance device possible at all. It is well known that strong high-frequency fields in the megahertz range as well as strong gradient fields in the low-frequency range are used in the magnetic resonance device for imaging. The EKG measurement may neither be disturbed by the operation of the magnetic resonance device nor may it disturb the operation of the magnetic resonance device itself. EKG measurement devices which are MR-compatible in the sense stated above are available on the market.

However the problem with such devices remains magnetic fields which change over time, as are used in the magnetic resonance device as magnetic gradient fields for location encoding. According to the law of induction, changes to magnetic fields over time create noise voltages which are coupled into the EKG signal received by the EKG electrodes as noise. Movements of the patient during image recording in the static magnetic field also create noise signals in accordance with the law of induction, because the effective surface for the coupling-in is changed by the movement. These types of magnetically-created noise signals overlay themselves with the EKG signal created by the body and falsify this signal.

Recording a magnetic resonance image synchronized with the heartbeat however basically demands a reliable detection of the R wave in the EKG signal. The noise signals generated by the switched gradient fields and also by rapid movements can however be mistakenly interpreted as an R wave and thus, because of the incorrect triggering that they generate, lead to a marked deterioration in the image quality. The practice of investigating the EKG signals in the trigger unit of the EKG measurement device for problems caused by magnetic fields is known. To this end the dynamics of the EKG signals are analyzed and evaluated as to whether the EKG signal involves an R wave to be detected or a fault. Incorrect triggering is still not excluded if the dynamics of the noise signal correspond to those of the R wave in the EKG signal.

SUMMARY OF THE INVENTION

The underlying object of the invention is now to specify an EKG measurement arrangement which allows reliable detection of magnetic field-related faults and for which the risk of emitting incorrect trigger signals is reduced.

The present object is achieved by the subject matter of the independent claim. The invention is based on the knowledge that magnetic field-related faults exhibit a large common-mode component in the EKG signal of the individual EKG electrodes. Accordingly the EKG measurement device comprises a number of EKG electrodes and a common-mode measurement unit which is connected on its input side to the EKG electrodes, with the common-mode measurement unit being connected on its output side to an EKG trigger unit. The trigger unit creates a trigger signal when it detects the R wave in the EKG signal. The common-mode signal generated by the common mode measurement unit in the case of magnetic field-related faults is fed to the trigger unit. The trigger unit then detects from the common-mode signal when the magnetic field-related faults are present and can thus avoid incorrect triggering. To this end the common-mode signal is detected together with the EKG signals and processed, e.g. subjected like the EKG signals to differentiation, signal matching, filtering and A/D conversion and evaluated in the trigger unit. If an appreciable common-mode signal appears, this means that a limit value has been undershot or exceeded and it is assumed that similar faults are also present in the parallel EKG signal. The outputting of the trigger signal is then for example, as is known in the prior art, blocked for the period during which the common-mode signal occurs.

An advantageous embodiment is characterized by common-mode measurement unit being linked via a subtractor to the EKG trigger unit and thus by the subtractor being linked on its input side to a further electrode. This means that the common-mode signal is related to the reference potential of the further electrode. The reference electrode is generally the RL electrode.

In a further, especially advantageous embodiment, the common-mode measurement unit is connected on its output side to a further electrode. A reference potential control, as already described at the outset, is realized by feedback to a further electrode in order to compensate for low-frequency faults.

A further, especially advantageous embodiment, is characterized by the common-mode measurement unit being connected via a subtractor to the EKG trigger unit, by the subtractor on its input side being connected to a further electrode and by the common-mode measurement unit being connected on its output side to the further electrode. Initially the feedback largely reduces the low-frequency magnetic field-related noise signals in the EKG signals. The remaining higher frequency noise signal is then analyzed in the EKG trigger unit together with the EKG signals in order to eliminate false trigger signals.

Further embodiments are characterized by the other subclaims.

BRIEF DESCRIPTION OF THE DRAWINGS

The invention is explained below on the basis of six figures. These are as follows.

DETAILED DESCRIPTION OF THE INVENTION

Figure 1:
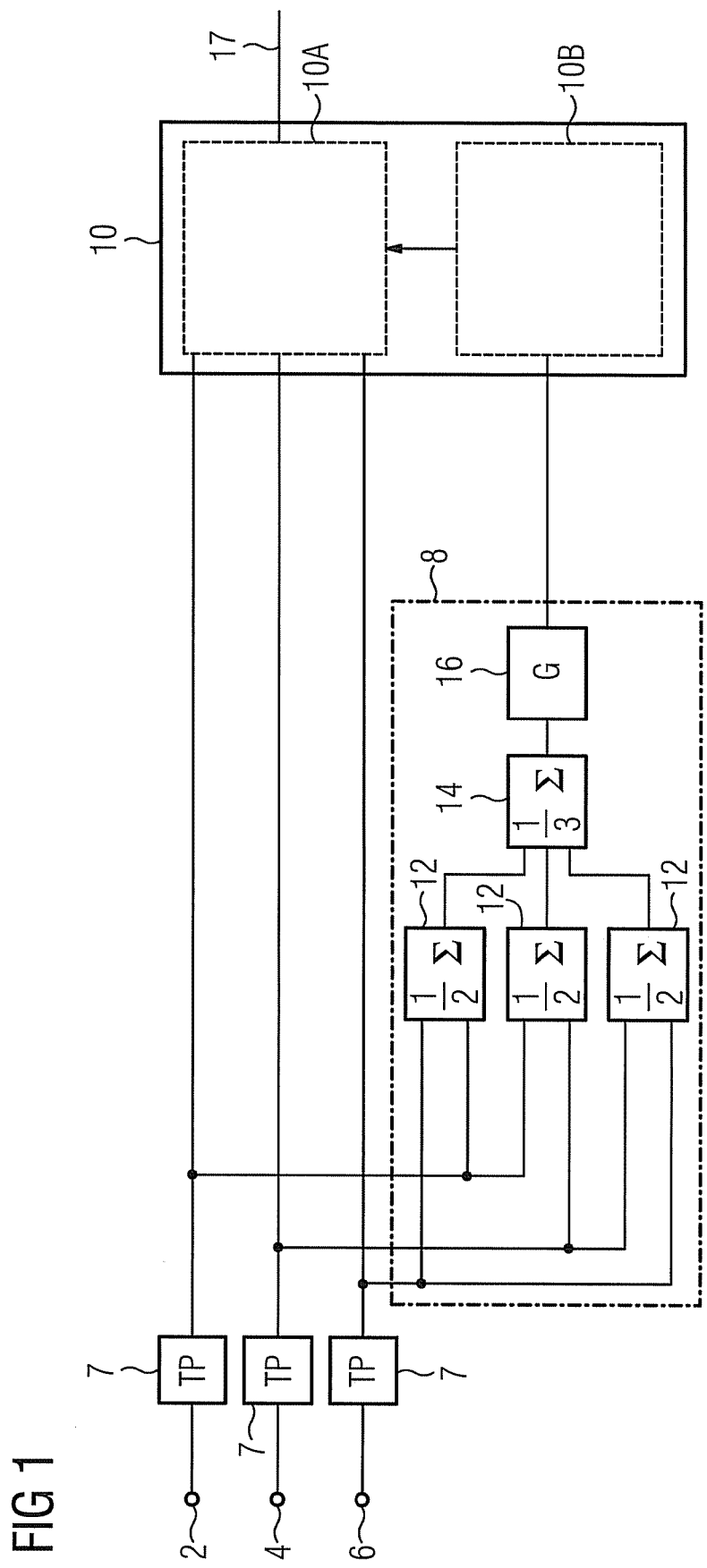
FIG. 1 a block diagram of the structure of a first EKG measurement device.

The first EKG measurement device shown in the block diagram in FIG. 1 comprises three electrodes 2, 4 and 6, which are stuck onto the surface of a patient's skin in accordance with a standard color coding in the traffic light scheme. Thus electrode 2 for example is stuck onto the right arm with the color coding red, electrode 4 to the left arm with the color coding yellow and electrode 6 to the left leg with the color coding green. Over time different so-called derivative schemes have developed. Particular reference is made here to the derivative scheme in accordance with Einthoven. In bipolar derivation according to Einthoven the electrical potential change is measured between the extremities. In this case Einthoven I stands for the potential difference between the left arm and the right arm, Einthoven II for the potential difference between the left leg and the right arm and Einthoven III for the potential difference between the left leg and the left arm. For examinations in the magnetic resonance the restriction applies that in general the electrodes 2, 4, 6 are not attached to the extremities themselves but to the thorax. It is also usual in this connection to attach four electrodes to the upper body at the corners of a rectangle around the heart. The transfer of the Einthoven derivative to the thorax is also referred to as chest wall derivative according to Nehb.

The electrodes 2, 4, 6 are connected via lowpass filters 7 with a limit frequency of appr. 130 Hz to a common-mode measurement unit 8 and to a trigger unit 10. The lowpass filters 7 block the high-frequency components from the EKG measurement signal which, because of user-specific high-frequency faults, are overlaid onto the electrophysiological signal.

The common-mode measurement unit 8 is constructed in two stages. The first stage comprises three mean value generators 12, the inputs of which are connected to two different electrodes 2, 4, 6 in each case. The mean value generators 12 create an arithmetic mean from the EKG measurement signals fed to their inputs. They thus include analog summators with an amplification factor of 0.5. The mean value signals created by the mean value generators 12 are fed in a second stage to a further mean value generator 14. The mean value generator 14 forms the arithmetic mean value of the mean value signals output by mean value generators 12, so that the mean value of all EKG signals and thereby the common-mode component of the EKG signals measured by the EKG electrodes are available as the output signals. A further signal amplification and where necessary also an impedance matching is undertaken in an amplifier stage 16 downstream from the mean value generator 14. Depending on the components used, the mean value generators 12 and 14 can also contain a signal amplifier stage.

Like the EKG signals, the common-mode signal output at the output of the amplifier 16 is fed to the EKG trigger unit 10. The EKG trigger unit comprises a trigger signal generator unit 10A and a control unit 10B. After reliable detection of the R wave the trigger signal generator unit 10A creates a trigger pulse in the EKG signal at an output 17. In the control unit 10B the dynamics and if necessary also the amplitude of the common-mode signal delivered by the amplifier 16 are analyzed and compared to reference values. If the two variables exceed specific limit values which are derived from the reference values, a message is output for example and the issuing of a trigger signal by the trigger signal generator unit 10A at output 17 is suppressed.

Figure 2:
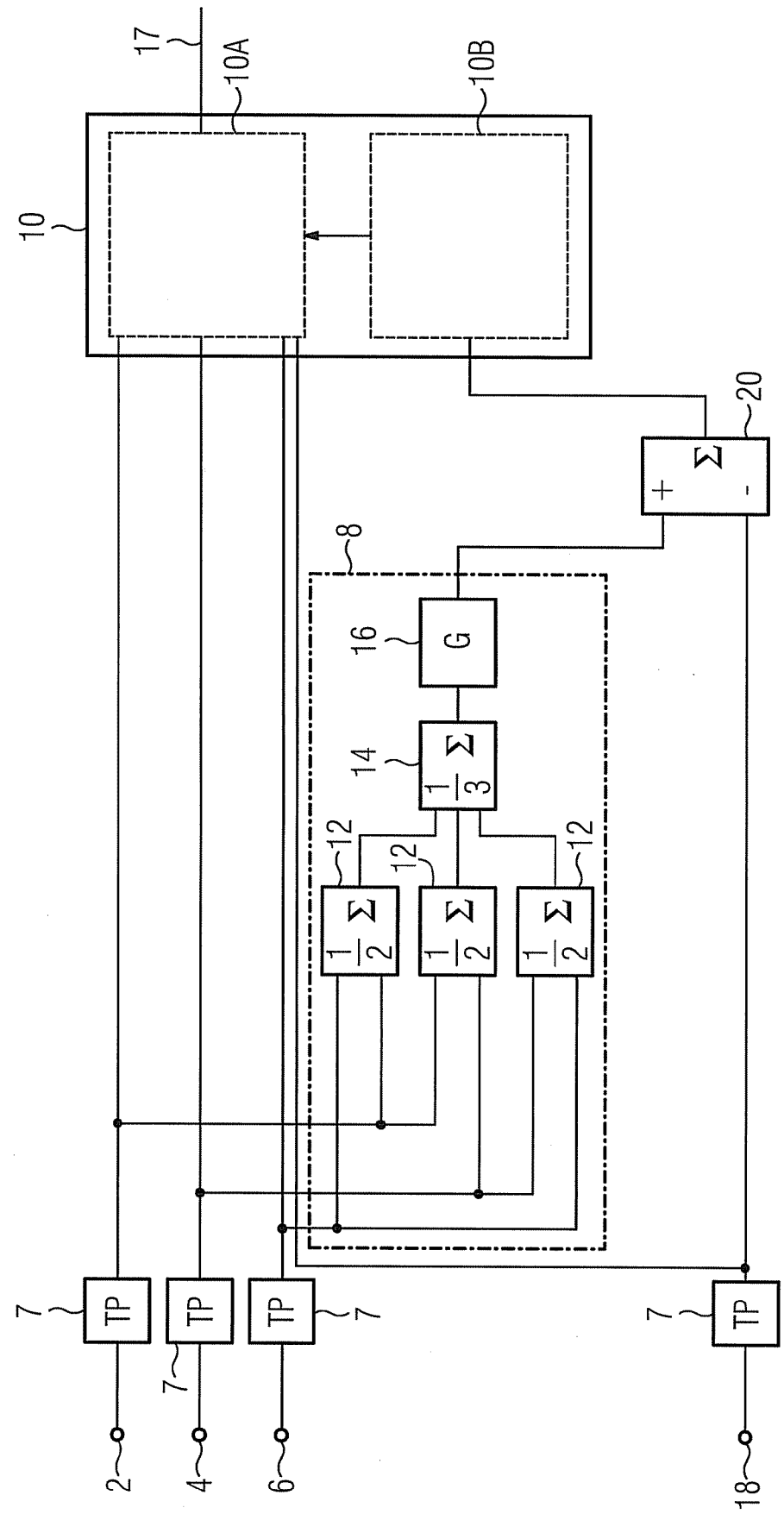
FIG. 2 a block diagram of the structure of a second EKG measurement device.

FIG. 2 shows in a block diagram of a second embodiment of the EKG measurement device, which differs from the EKG measurement device shown in FIG. 1 in that a further electrode 18 is provided as a reference electrode. The reference electrode 18, when a total of 4 electrodes are placed in a rectangle around the heart, is to be placed at the corner closest to the shoulder.

The reference electrode 18 is connected via a lowpass 7 with a limit frequency of appr. 130 Hz to the control unit 10B and to a minus input of a subtractor 20. The common-mode signal from the common-mode measurement unit 8 is fed to the plus input of the subtractor 20. This signal processing means that the common-mode signal of the EKG electrodes 2, 4, 6 is merely fed as a difference potential to reference electrode 18 of the trigger unit 10. This creates an advantageous reference to the body potential.

The further processing and evaluation in the EKG trigger unit 10 is undertaken in the same manner as has already been described with reference to FIG. 1.

Figure 3:
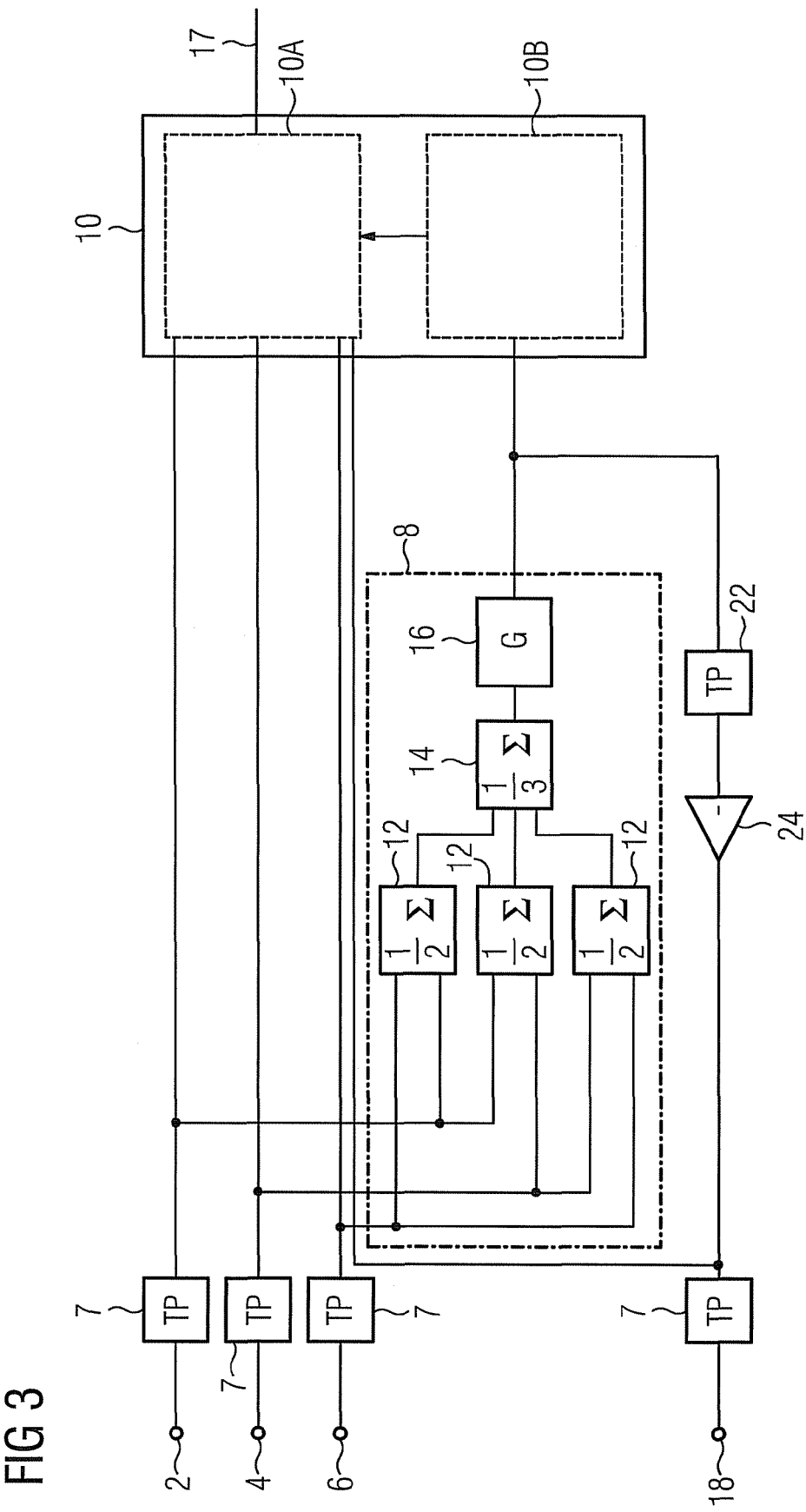
FIG. 3 a block diagram of the structure of a third EKG measurement device.

FIG. 3 shows a further EKG measurement arrangement, which likewise proceeds from the EKG measurement arrangement depicted in FIG. 1. Here too the reference electrode 18 is connected via the lowpass filter 7 to the control unit 10A. The common-mode signal generated by the common-mode measurement unit 8 is in this case additionally fed via a lowpass filter 22 and an inverter 24 via the lowpass filter 7 to the reference electrode 18. The lowpass filter 22 is designed to feed back low-frequency faults to allow compensation processes in the body. This external feedback means that magnetic symmetrical coupled-in low-frequency interference signals are already compensated for in the EKG signal at all EKG electrodes 2, 4 and 6. Remaining high-frequency residual noise signals are then, as already described with reference to FIG. 1, analyzed and further processed in the EKG trigger unit 10.

Figure 4:
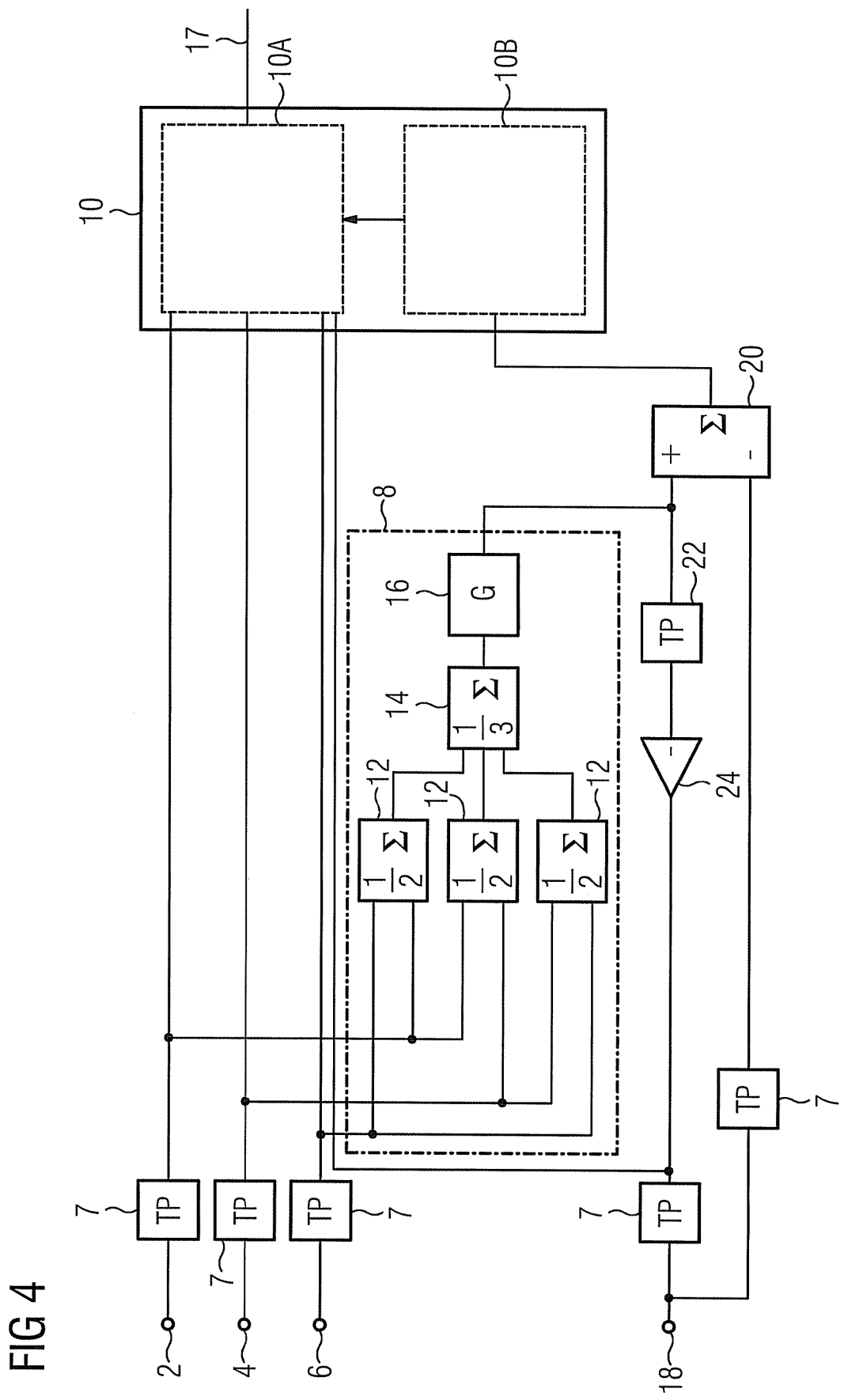
FIG. 4 a block diagram of the structure of a fourth EKG measurement device.

The fourth exemplary embodiment of an inventive EKG measurement device shown in FIG. 4 comprises both feeding back, as described in FIG. 3, and also the differentiation of the common-mode signal from the signal received by the reference electrode 18 described with reference to FIG. 2. Here too the reference electrode 18 is connected via the lowpass filter 7 to the control unit 10A. The lowpass 7 blocks MR-specific high-frequency faults.

Figure 5:
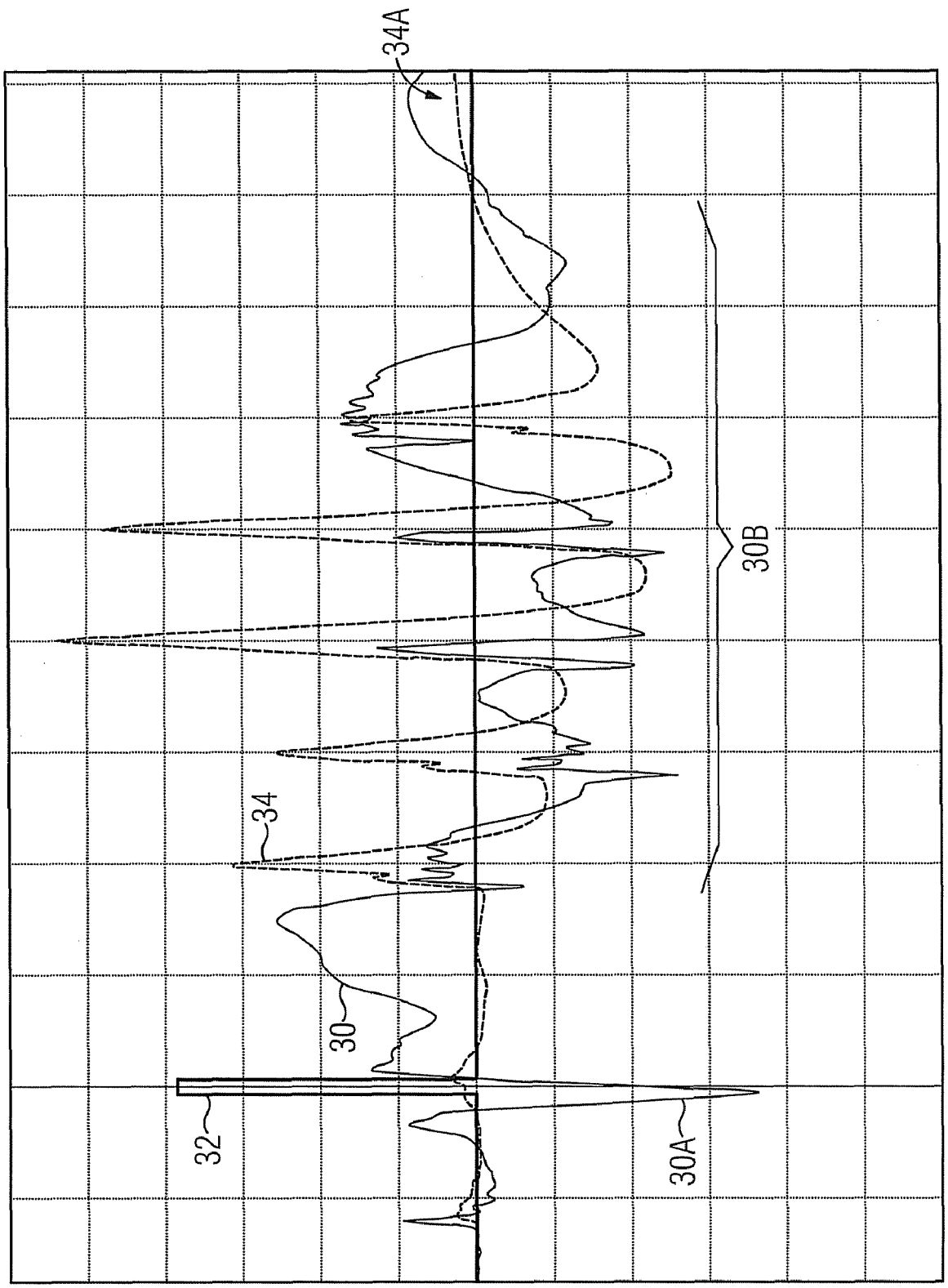
FIG. 5 to illustrate the timing of a disrupted EKG measurement signal as well as the common -mode signal detected simultaneously as a noise signal, and FIG. 6 an overview diagram of a diagnostic magnetic resonance device with an integrated trigger unit.

To illustrate the functioning of the EKG measurement device described here, FIG. 5 shows the signal waveform of an EKG-signal 30 over time, as generated as a phase difference signal for example from the EKG signals tapped off from electrodes 2 and 4. In EKG signal 30 an R wave 30A can clearly be seen, after which a trigger pulse 32 is created. In the further course 30B of the EKG signal 30 however a magnetically coupled-in fault occurs which no longer allows the R wave to be securely detected. This fault is clearly shown in the common-mode signal 34. As soon as the common-mode signal 34 has a specific amplitude and dynamic, the creation of trigger signals 32 is blocked. After the common-mode signal 34 decays and after a specific wait time if necessary, trigger signal generation is enabled again in area 34A.

Figure 6:
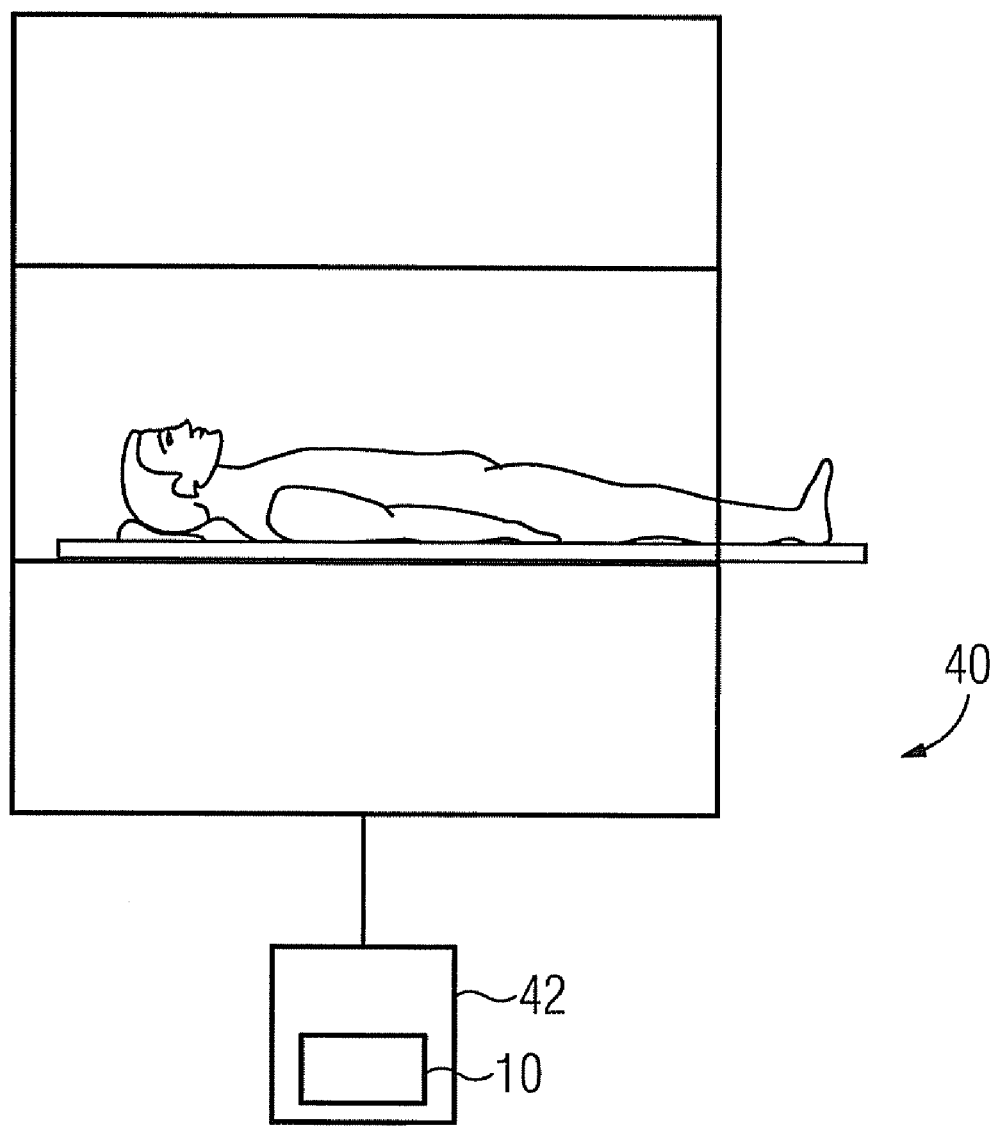

FIG. 6 shows in an overview diagram a diagnostic magnetic resonance device 40 with an integrated EKG trigger unit 10. There are two particular advantages associated with such a device. On the one hand the EKG trigger unit can be implemented as software and can run on a control processor 42 of the MR device 40. This means that the high computing power in the MR device 40 is also available for the EKG trigger unit 10. On the other hand the EKG trigger unit 10 can access MR device parameters and MR process variables in a simple and fast manner.

The invention claimed is:

1. An EKG measurement device, comprising:
    an EKG electrode that generates an EKG signal of a patient;
    a common-mode measurement unit with an input side connected to the EKG electrode that generates a common mode signal based on the EKG signal; and
    an EKG trigger unit with an input side connected to the EKG electrode and to the common-mode measurement unit that detects the common mode signal and triggers the EKG measurement device based on the detection,
    wherein the EKG electrode is connected to the common-mode measurement unit via a lowpass filter.

2. The EKG measurement device as claimed in claim 1, wherein the EKG trigger unit comprises a trigger signal generator unit that generates a trigger signal based on the EKG signal.

3. The EKG measurement device as claimed in claim 2, wherein the EKG trigger unit comprises a control unit that controls the trigger signal generation unit based on the common mode signal.

4. The EKG measurement device as claimed in claim 1,
    wherein the common-mode measurement unit is connected to the EKG trigger unit via a subtractor, and
    wherein an input side of the subtractor is connected to a further electrode.

5. The EKG measurement device as claimed in claim 1, wherein an output side of the common-mode measurement unit is connected to a further electrode.

6. The EKG measurement device as claimed in claim 1,
    wherein the common-mode measurement unit is connected to the EKG trigger unit via a subtractor,
    wherein an input side of the subtractor is connected to a further electrode, and
    wherein an output side of the common-mode measurement unit is connected to the further electrode.

7. The EKG measurement device as claimed in claim 1, wherein an inverter is inserted between the common-mode measurement unit and a further electrode.

8. The EKG measurement device as claimed in claim 1, wherein the common-mode measurement unit is connected to a further electrode via a further lowpass filter.

9. The EKG measurement device as claimed in claim 1, wherein the common-mode measurement unit comprises an amplifier.

10. The EKG measurement device as claimed in claim 1, wherein the EKG measurement device is configured to be used during a magnetic resonance image of the patient.

* * * * *